United States Patent [19] [11] 4,230,637
Zander [45] Oct. 28, 1980

[54] PROCESS FOR THE PREPARATION OF CHLORINE-SUBSTITUTED AROMATIC AMINES

[75] Inventor: Jürgen Zander, Leverkusen, Fed. Rep. of Germany

[73] Assignee: Bayer Aktiengesellschaft, Leverkusen, Fed. Rep. of Germany

[21] Appl. No.: 941,098

[22] Filed: Sep. 8, 1978

[30] Foreign Application Priority Data

Sep. 28, 1977 [DE] Fed. Rep. of Germany ....... 2743610

[51] Int. Cl.$^2$ .............................................. C07C 85/11
[52] U.S. Cl. ................................................... 260/580
[58] Field of Search .......................................... 260/580

[56] References Cited

U.S. PATENT DOCUMENTS 3,868,403  2/1975  Becker et al. ..................... 260/580 X
4,070,401  1/1978  Hirai et al.

FOREIGN PATENT DOCUMENTS 48-49729  7/1973  Japan ....................................... 260/580

Primary Examiner—John Doll
Attorney, Agent, or Firm—Sprung, Felfe, Horn, Lynch & Kramer

[57] ABSTRACT

An improved process for the preparation of a chlorinated aromatic amine by reaction of a chlorinated aromatic nitro compound of the formula

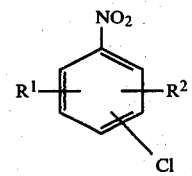

wherein $R^1$ and $R^2$ are identical or different and denote hydrogen or chlorine with hydrogen in the presence of a hydrogenation catalyst under pressure at an elevated temperature in the presence of a solvent and a minor amount of a basic compound, the improvement residing in employing ammonia as the basic compound.

8 Claims, 1 Drawing Figure

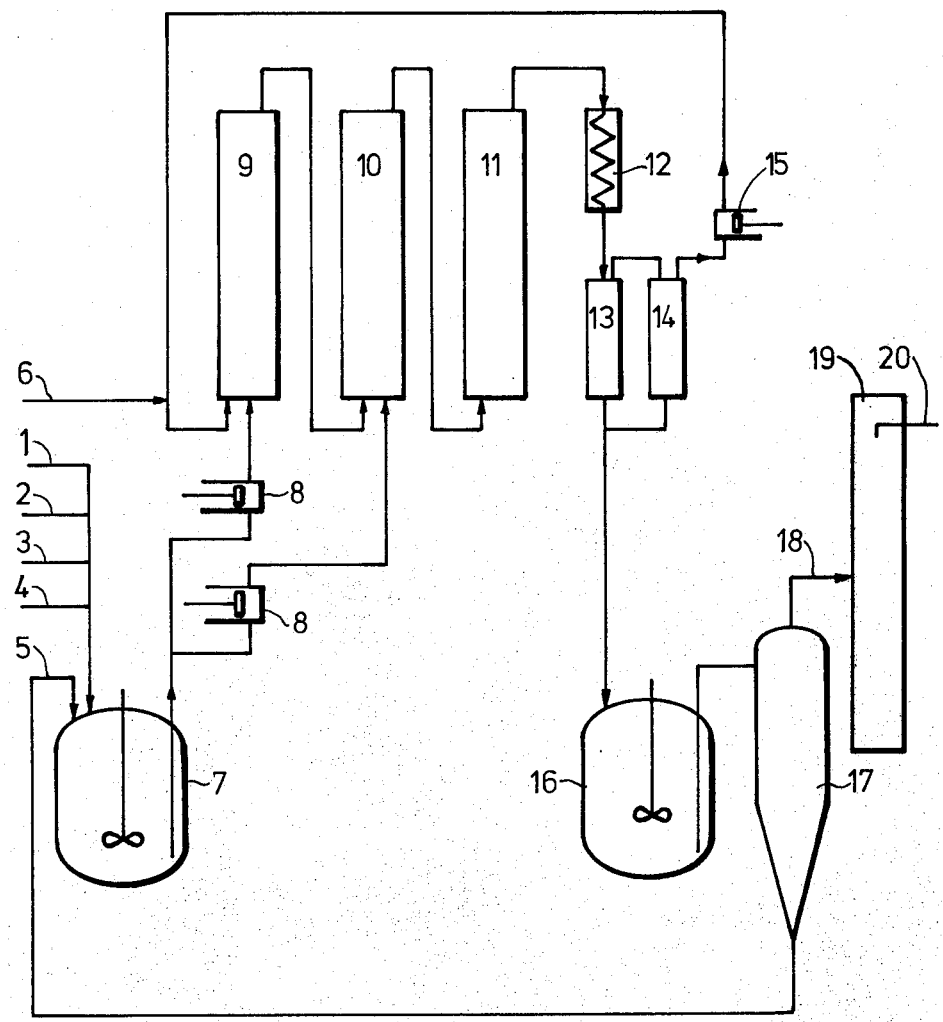

PROCESS FOR THE PREPARATION OF CHLORINE-SUBSTITUTED AROMATIC AMINES

The invention relates to a process for the preparation of chlorine-substituted aromatic amines.

It is known to prepare chlorine-substituted aromatic amines by hydrogenating the corresponding nitro compounds in the presence of noble metal catalysts (Ullmann, volume 7, 4th edition, page 570 et seq. (1973)).

It is also known to carry out the reaction in the presence of basic compounds such as, for example, calcium carbonate (DT-AS (German Published Specification) No. 1,125,436, U.S. Pat. No. 3,051,753 and DT-OS (German Published Specification) No. 1,493,629) or amines, for example morpholine (DT-AS (German Published Specification) No. 1,187,243, U.S. Pat. No. 3,291,832, U.S. Pat. No. 3,361,819 and U.S. Pat. No. 3,499,030) and methyl amine (DOS 1 193 498).

A process has been found for the preparation of chlorinated aromatic amines by reacting chlorinated aromatic nitro compounds of the formula

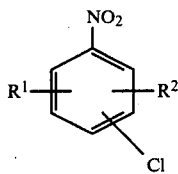

(I)

wherein
$R^1$ and $R^2$ are identical or different and denote hydrogen or chlorine,
with hydrogen under pressure at an elevated temperature in the presence of a solvent and of small amounts of a basic compound, characterised in that ammonia is employed as the basic compound.

Compounds which can preferably be employed as chlorinated aromatic nitro compounds for the process according to the invention are those of the formula

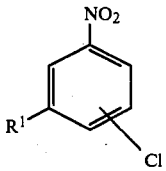

(II)

wherein
$R^1$ has the abovementioned meaning.

The following chlorinated aromatic nitro compounds may be mentioned as examples: o-chloronitrobenzene, m-chloronitrobenzene, p-chloronitrobenzene, 2,4-dichloro-nitrobenzene, 2,5-dichloro-nitrobenzene, 3,4-dichloro-nitrobenzene, 2,3,5-trichloro-nitrobenzene and 2,4,6-trichloro-nitrobenzene.

Of course it is possible to employ mixtures of the chlorinated aromatic nitro compounds in the process according to the invention.

The process according to the invention is in general carried out in the temperature range of 120° to 160° C., preferably of 130° to 150° C., and in the pressure range of 50 to 250 bars, preferably 80 to 130 bars.

Examples which may be mentioned of solvents for the process according to the invention are lower aliphatic alcohols, such as methanol, ethanol, propanol, isopropanol, butanol, isobutanol, pentanol, isopentanol, hexanol and isohexanol, preferably isopropanol, and aromatic solvents, such as benzene, toluene and xylene, preferably toluene.

According to the process of the invention, ammonia is employed as the basic compound. The ammonia may be employed either as a gas or in solution.

As ammonia solutions, both aqueous solutions and solutions in one of the abovementioned solvents for the process according to the invention may be mentioned.

In general, a concentration of 0.2 to 5 parts by weight, preferably 0.3 to 3 parts by weight, and especially preferentially 0.70 to 1.5 parts by weight, of ammonia, relative to 100 parts by weight of the chlorinated aromatic nitro compounds, is maintained in the reaction mixture in the process according to the invention.

Hydrogenation catalysts for the process according to the invention are in themselves known (Ullmann, volume 7, 4th edition, page 570 et seq. (1973)).

The following hydrogenation catalysts may be mentioned as examples: platinum on a charcoal carrier, platinum on a carrier of barium carbonate and/or strontium carbonate, rhodium on a charcoal carrier, and Raney nickel.

The process according to the invention can be carried out discontinuously or continuously.

An embodiment of the process according to the invention will be explained, by way of example, with the aid of FIG. 1;

The chlorinated aromatic nitro compound, the solvent, the ammonia and the catalyst are introduced through the feedlines (1) to (4) and are mixed in the kettle (7) with the reaction mixture which is present in the process circulation and which is introduced into the kettle (7) through (5). The mixture is then introduced, by means of high pressure pumps (8) into the reactor (9) or, in the case of multi-reactor systems, into all reactors with the exception of the last post-reactor, and is there reacted with hydrogen (6) which is introduced into the reactor (9) together with the circulating hydrogen. The heat of reaction is removed by means of the cooling water. The product leaving the reactors is cooled in the cooler (12) and is separated from the gas phase in the product separators (13 and 14), the gas phase being returned to the first reactor by means of the circulating pump (15). The solution of the chlorinated aromatic amines discharged from the high pressure chamber by means of regulating valves is degassed in the kettle (16) and then freed from the catalyst in the filter (17). The chlorinated aromatic amine is withdrawn from the circulation through (18). A part of the reaction mixture is withdrawn at the bottom of the filter 17. The solvent together with the ammonia is distilled from the filtrate by means of a distillation column and is returned to the kettle (7) via the intermediate tank (5).

The known basic compounds for carrying out the hydrogenation of chlorine-substituted aromatic nitro compounds have the disadvantage that they can only be separated with difficulty from the end product and require expensive purification operations.

It is an advantage that according to the process of the invention the ammonia can be separated off easily.

It is an advantage that the process according to the invention can be carried out even at high throughputs and high temperatures virtually without the formation of by-products. It is a further advantage that virtually no dechlorination of the starting material occurs. When carrying out the process according to the invention industrially, the ease of metering and the ease of distributing the ammonia in the reaction mixture are of advantage.

Using the process according to the invention, it is possible to prepare chlorinated aromatic amino compounds of the formula

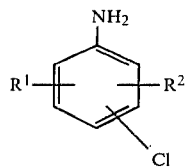
(III)

wherein
$R^1$ and $R^2$ have the abovementioned meaning.

The following chlorinated aromatic amino compounds may be mentioned by way of examples: o-, m- and p-chloroaniline, 3,4- and 2,5-dichloroaniline and 4-chloronitrotoluene.

The chlorinated aromatic amines are intermediates for plant protection agents and dyes.

EXAMPLES:

The reaction apparatus employed in Examples 1 to 3 will be explained with the aid of FIG. 1:

The reaction apparatus consists of three tubular reactors (9, 10, 11) arranged in series and provided with cooling pipes to remove the heat of reaction, the product cooler (12), the separators (13 and 14) and the gas circulation pump (15), by means of which a circulation of hydrogen is set up.

In continuous operation, the chlorinated aromatic nitro compound, the solvent, the ammonia and the catalyst are introduced through the feedlines (1 to 4) and are mixed in the kettle (7), with the reaction mixture (5) which is present in the process circulation and which contains catalyst. The mixture is then fed into the reactor (9) by means of high pressure pumps (8) and is there reacted with hydrogen (6) which is introduced into the reactor (9) together with the circulating hydrogen. The heat of reaction is removed by means of cooling water. The product leaving the reactors is cooled in the cooler (12) and is separated, in the separators (13 and 14), from the circulating gas, which is returned to the first reactor by means of the circulating pump (15). The amine solution discharged from the high pressure chamber by means of regulating valves is separated from the hydrogen in the kettle (16) and subsequently freed from the catalyst in the filter (17); the amine solution is taken off through the outlet (18). The solvent, together with the ammonia, is distilled off (20) from the clear filtrate in a distillation column (19) and returned to the kettle (7) via an intermediate tank. The catalyst which remains in returned, with a part of the reaction mixture present in the process circulation, to the kettle (7) through (5).

EXAMPLE 1

Per hour, 3,000 kg of 3,4-dichloronitrobenzene, 4,200 kg of isopropane-water azeotrope ($H_2O$ content about 15% by weight), 4 kg of ammonia and 2,000 kg of finished product solution containing catalyst are pumped continuously into the reactors of a system consisting of two main reactors and a post-reactor. The circulating material contains 1 to 2% of catalyst (1% strength platinum on charcoal).

The hydrogen pressure is kept at 100 bars and the temperature is kept at 130° to 145° C. by means of cooling water. The product leaving the reactors has been converted completely and is free from nitro compounds.

The pH value of the finished amine solution should be between 9 and 12. The amount of ammonia added per hour is increased or decreased in accordance with the change in pH value which occurs.

The isopropanol-water mixture recovered by distillation can be re-used without purification. The crude 3,4-dichloroaniline which has been substantially freed from water and is virtually colourless (yield 99% of theory) has a solidification point of 71.5° to 71.6° C.

EXAMPLE 2

If 2,5-dichloronitrobenzene is hydrogenated analogously to Example 1, 2,5-dichloro-aniline is obtained in a yield of 99% of theory.

EXAMPLE 3

If o-chloronitrobenzene is hydrogenated analogously to Example 1, o-chloro-aniline is obtained in a yield of 99% of theory.

What is claimed is:

1. In a process for the preparation of a chlorinated aromatic amine by contacting a chlorinated aromatic nitro compound of the formula

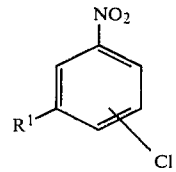

wherein $R^1$ and $R^2$ are identical or different and denote hydrogen or chlorine with hydrogen in the presence of a hydrogenation catalyst under a pressure at elevated temperature in the presence of a solvent and a small amount of a basic compound, the improvement wherein said basic compound is ammonia, said ammonia being present in an amount of from 0.2 to 5 parts by weight per 100 parts by weight of said chlorinated aromatic nitro compound and said hydrogenation catalyst is a platinum hydrogenation catalyst.

2. A process according to claim 1 wherein the ammonia is employed in an amount of 0.3 to 5 parts by weight relative to 100 parts by weight of a chlorinated aromatic nitro compound.

3. A process according to claim 1 wherein the ammonia is employed in the form of a solution.

4. A process according to claim 3 wherein ammonia is employed in the form of an aqueous solution.

5. A process according to claim 1 wherein said chlorinated aromatic nitro compound is selected from the group consisting of o-chloronitrobenzene, m-chloronitrobenzene, p-chloronitrobenzene, 2,4-dichloro-nitrobenzene, 2,5-dichloro-nitrobenzene, 3,4-dichloronitrobenzene, 2,3,5-trichloro-nitrobenzene and 2,4,6-trichloro-nitrobenzene.

6. A process according to claim 1 wherein the reaction is carried out at a temperature in the range of 120° to 160° C. at a pressure in the range of 50 to 250 bars.

7. A process according to claim 3 wherein the solvent is a lower aliphatic alcohol or an aromatic solvent.

8. A process according to claim 7 wherein the solvent is selected from the group consisting of methanol, ethanol, propanol, isopropanol, butanol, isobutanol, pentanol, isopentanol, hexanol and isohexanol, benzene, toluene and xylene.

* * * * *